(12) United States Patent
Yeoman et al.

(10) Patent No.: US 9,839,212 B2
(45) Date of Patent: Dec. 12, 2017

(54) MULTICOMPONENT AND MULTILAYER COMPACTED TABLETS

(71) Applicant: Bio-Lab, Inc., Lawrenceville, GA (US)

(72) Inventors: Alan Yeoman, Duluth, GA (US);
Curtis Sayre, Atlanta, GA (US);
Edward Santorella, Canton, GA (US)

(73) Assignee: Bio-Lab, Inc., Lawrenceville, GA (US)

( * ) Notice: Subject to any disclaimer, the term of this patent is extended or adjusted under 35 U.S.C. 154(b) by 0 days.

(21) Appl. No.: 14/687,955

(22) Filed: Apr. 16, 2015

(65) Prior Publication Data

US 2016/0302410 A1    Oct. 20, 2016

(51) Int. Cl.
| | | |
|---|---|---|
| *A01N 25/34* | (2006.01) | |
| *B30B 11/04* | (2006.01) | |
| *B30B 15/30* | (2006.01) | |
| *A01N 43/66* | (2006.01) | |
| *A61K 9/20* | (2006.01) | |

(52) U.S. Cl.
CPC ............. *A01N 25/34* (2013.01); *A01N 43/66* (2013.01); *B30B 11/04* (2013.01); *B30B 15/306* (2013.01); *A61K 9/2086* (2013.01)

(58) Field of Classification Search
None
See application file for complete search history.

(56) References Cited

U.S. PATENT DOCUMENTS

| | | | |
|---|---|---|---|
| 3,063,390 A | 11/1962 | Frank | |
| 3,158,109 A | 11/1964 | Stott | |
| 4,167,380 A * | 9/1979 | Stuben | B30B 15/306 425/134 |
| 4,828,749 A | 5/1989 | Kruse et al. | |
| D324,935 S | 3/1992 | Copp | |
| D335,330 S | 5/1993 | Gladfelter et al. | |
| 5,213,738 A * | 5/1993 | Hampton | A61J 3/10 264/112 |
| 5,217,639 A | 6/1993 | Mottola | |
| D344,154 S | 2/1994 | Mottola | |
| 5,534,263 A | 7/1996 | Wong et al. | |
| 5,609,884 A | 3/1997 | Desai | |
| 5,626,874 A | 5/1997 | Conte et al. | |
| 5,667,804 A | 9/1997 | Wong et al. | |
| D387,537 S | 12/1997 | Fosher | |
| 5,738,874 A | 4/1998 | Conte et al. | |
| 5,750,061 A | 5/1998 | Farina et al. | |
| 5,753,602 A | 5/1998 | Hung et al. | |
| 5,912,012 A | 6/1999 | Carlin et al. | |
| 5,958,853 A | 9/1999 | Watanabe | |
| 5,962,387 A | 10/1999 | Gorlin et al. | |
| D419,261 S | 1/2000 | Binstock et al. | |
| D420,464 S | 2/2000 | Binstock et al. | |
| D420,763 S | 2/2000 | Forward et al. | |
| 6,020,000 A | 2/2000 | Wong et al. | |
| 6,051,545 A | 4/2000 | Boskamp | |
| D427,415 S | 7/2000 | Dolphin | |
| D430,344 S | 8/2000 | van der Hagen | |
| D430,345 S | 8/2000 | van der Hagen | |
| D430,346 S | 8/2000 | van der Hagen | |
| 6,183,778 B1 | 2/2001 | Conte et al. | |
| 6,183,779 B1 | 2/2001 | Quali et al. | |
| 6,194,368 B1 | 2/2001 | Waschenbach et al. | |
| 6,235,127 B1 | 5/2001 | Rader et al. | |
| 6,287,600 B1 | 9/2001 | Quali et al. | |
| 6,306,814 B1 | 10/2001 | Appel et al. | |
| 6,313,080 B1 | 11/2001 | Boskamp et al. | |
| 6,316,028 B1 | 11/2001 | Wong et al. | |
| 6,339,059 B1 | 1/2002 | Appel et al. | |
| 6,358,910 B1 | 3/2002 | Boskamp et al. | |
| 6,376,441 B1 | 4/2002 | Ross et al. | |
| 6,426,317 B1 | 7/2002 | Garris et al. | |
| D486,733 S | 2/2004 | Murning et al. | |
| 6,702,803 B2 | 3/2004 | Kupperblatt et al. | |
| D500,849 S | 1/2005 | Rinker et al. | |
| 6,852,238 B2 | 2/2005 | Connelly, Jr. | |
| 6,863,830 B1 | 3/2005 | Purdy et al. | |
| D524,479 S | 7/2006 | Bourgoin et al. | |
| D536,824 S | 2/2007 | Karussi et al. | |
| D536,825 S | 2/2007 | Jekel et al. | |
| D549,871 S | 8/2007 | Karussi et al. | |
| D550,833 S | 9/2007 | Stawski et al. | |
| 7,309,444 B2 | 12/2007 | Connelly, Jr. | |
| D562,496 S | 2/2008 | Wiedemann | |
| D563,598 S | 3/2008 | Wiedemann | |
| D565,243 S | 3/2008 | Denome et al. | |
| D566,894 S | 4/2008 | Wiedemann | |
| D567,998 S | 4/2008 | Wiedemann | |
| D599,057 S | 8/2009 | Beckholt et al. | |
| D601,689 S | 10/2009 | Karolak et al. | |
| D610,674 S | 2/2010 | Karolak et al. | |
| D610,675 S | 2/2010 | Larsen et al. | |
| D612,478 S | 3/2010 | Karolak et al. | |
| 7,807,197 B2 | 10/2010 | Lee et al. | |
| D631,537 S | 1/2011 | Sadler et al. | |

(Continued)

FOREIGN PATENT DOCUMENTS

| | | |
|---|---|---|
| DE | 12 30 523 B | 12/1966 |
| EP | 0 316 479 A1 | 5/1989 |

(Continued)

OTHER PUBLICATIONS

Gopinath et al.; "An Overview on Bilayered Tablet Technology"; Journal of Global Trends in Pharmaceutical Sciences; Bolume 4, Issue 2, pp. 1007-1085; Apr.-Jun. 2013; available online at www.JGTPS.com; 10 pgs.

(Continued)

*Primary Examiner* — Susan Tran (74) *Attorney, Agent, or Firm* — Merchant & Gould P.C.

(57) ABSTRACT

Horizontally layered tablets, methods of making the horizontally layered tablets, and tableting equipment capable of producing the horizontally layered tablets are described. The horizontally layered tablets can be produced by simultaneously feeding a segregated flow of different compositions that form the respective layers of the tablet.

1 Claim, 4 Drawing Sheets

(56) References Cited

U.S. PATENT DOCUMENTS

| | | | |
|---|---|---|---|
| D632,843 S | 2/2011 | Wilson et al. |
| 7,879,354 B2 | 2/2011 | Rinker et al. |
| D639,183 S | 6/2011 | Nixon |
| D639,184 S | 6/2011 | Nixon |
| D640,934 S | 7/2011 | Nixon |
| 7,985,427 B2 | 7/2011 | Solomonidou et al. |
| 7,988,996 B2 | 8/2011 | Solomon et al. |
| 8,034,380 B2 | 10/2011 | Solomon et al. |
| 8,067,029 B2 | 11/2011 | Rinker et al. |
| D652,165 S | 1/2012 | Gordon et al. |
| D662,656 S | 6/2012 | Nixon |
| D662,658 S | 6/2012 | Nixon |
| D662,659 S | 6/2012 | Nixon |
| D663,069 S | 7/2012 | Nixon |
| 8,231,902 B2 | 7/2012 | Solomon et al. |
| 8,329,477 B2 | 12/2012 | Groepler |
| D683,499 S | 5/2013 | Dedeyan et al. |
| 8,492,419 B2 | 7/2013 | Feldman et al. |
| D691,326 S | 10/2013 | Gerhards |
| D695,451 S | 12/2013 | Gerhards |
| 8,663,496 B2 | 3/2014 | Branlard et al. |
| 2004/0071592 A1* | 4/2004 | Annis ............... A01N 35/04 422/36 |
| 2004/0156902 A1 | 8/2004 | Lee et al. |
| 2005/0019407 A1 | 1/2005 | Sowden et al. |
| 2007/0190133 A1 | 8/2007 | Bunick et al. |
| 2008/0153779 A1 | 6/2008 | Liao et al. |
| 2008/0187581 A1 | 8/2008 | Gore et al. |
| 2010/0239668 A1 | 9/2010 | Kaplan et al. |
| 2011/0300208 A1 | 12/2011 | Solomon et al. |
| 2012/0171287 A1 | 7/2012 | Jiang et al. |
| 2013/0243857 A1 | 9/2013 | Oliyai et al. |
| 2013/0292884 A1 | 11/2013 | Anderson et al. |
| 2013/0295174 A1 | 11/2013 | Sowden et al. |
| 2013/0295211 A1 | 11/2013 | Stuhl et al. |
| 2014/0005600 A1 | 1/2014 | Cho et al. |
| 2014/0056979 A1 | 2/2014 | Huang |

FOREIGN PATENT DOCUMENTS

| | | |
|---|---|---|
| JP | S58 44997 A | 3/1983 |
| WO | WO 2012/039788 A1 | 3/2012 |
| WO | WO 2013/001516 | 1/2013 |
| WO | WO 2013/166136 | 11/2013 |

OTHER PUBLICATIONS

International Search Report & Written Opinion, dated Aug. 12, 2016 cited in PCT/US2016/027423, 13 pages.

* cited by examiner

MULTICOMPONENT AND MULTILAYER COMPACTED TABLETS

TECHNICAL FIELD

The present invention is generally directed to horizontally layered tablets, methods of making the horizontally layered tablets, and tableting equipment capable of producing the horizontally layered tablets.

BACKGROUND

Traditional multilayer compacted tablets often are produced by the sequential addition of the separated components into a tablet die cavity using separate component gravity feed or force feed delivery devices to form the separate layers. Punch position changes may be required to form the desired layer at each component delivery device. In addition, there may be pre-compression of previously introduced layers, prior to the addition of subsequent layers, until a final compression is used to form a single multilayer tablet in which the separated components are arranged into vertical layers. Hence, such conventional tableting techniques are directed to vertically layered tablets, and the use of multiple compression or compaction steps results in reduced production rates.

The production of vertically layered tablets requires the use of tablet presses which have been purposely designed to produce multilayer tablets, or single layer tablet presses that have been significantly modified. Either option increases manufacturing complexity and equipment costs compared to single layer tablet presses. In addition to equipment complexity and cost, the production rate of multilayer tablets, as mentioned above, is often significantly slower than the production rate of single layer tablets.

Therefore, there is a need to develop processes to manufacture combined, separated components into a single compacted tablet form without the increased complexity, increased equipment cost, and reduced production rates associated with conventional multilayer tablet production. There is also a need to develop processes to manufacture combined, separated components into a single compacted tablet form (that is distinct from tablets with vertically arranged layers) in which horizontally arranged layers are formed in order to add aesthetic options to the products being produced, as well as to provide product performance enhancements associated with horizontal layer orientation.

Accordingly, it is to these ends, as well as other benefits, that the various aspects and embodiments consistent with this invention are directed.

SUMMARY

This summary is provided to introduce a selection of concepts in a simplified form that are further described below in the detailed description. This summary is not intended to identify required or essential features of the claimed subject matter. Nor is this summary intended to be used to limit the scope of the claimed subject matter.

The present invention is generally directed to compacted, horizontally layered tablets containing two more layers. In one aspect, a horizontally layered tablet can comprise a first layer, a second layer, and an interface between the first layer and the second layer. This tablet can be characterized, for example, by a density of at least about 1.2 g/cc. In another aspect, a horizontally layered tablet can comprise a first layer comprising a first composition, a second layer comprising a second composition, and an interface between the first layer and the second layer. Typically, the first composition and the second composition can be different. In these and other aspects, the width (or horizontal dimension, e.g., diameter if circular) of the tablet can be greater than the height (or vertical dimension) of the tablet, such as, for example, by a ratio of the width of the tablet to the height of the tablet ranging from about 1.2:1 to about 10:1, or from about 1.5:1 to about 5:1.

Other aspects of this invention are directed to methods of making a horizontally layered tablet, the horizontally layered tablet having a first layer and a second layer. One such method can comprise providing a first composition and a second composition, simultaneously feeding (not sequentially feeding) a segregated flow of the first composition and the second composition to a tablet die, and compressing the first composition and the second composition under sufficient pressure in the tablet die to form the horizontally layered tablet. In this method, the first layer comprises the first composition and the second layer comprises the second composition.

Further aspects of this invention are directed to suitable multilayer tableting equipment. For instance, an apparatus for forming a horizontally layered tablet having a first layer comprising a first composition and a second layer comprising a second composition is provided herein. This apparatus can comprise a tablet die, a first feed chamber containing the first composition and a second feed chamber containing the second composition, a reciprocating and segmented feed device for simultaneously directing a segregated flow of the first composition from the first feed chamber and the second composition from the second feed chamber to the tablet die, and a compaction device for compressing the first composition and the second composition in the tablet die under sufficient pressure to form the horizontally layered tablet having the first layer and the second layer.

Both the foregoing summary and the following detailed description provide examples and are explanatory only. Accordingly, the foregoing summary and the following detailed description should not be considered to be restrictive. Further, features or variations may be provided in addition to those set forth herein. For example, certain aspects and embodiments may be directed to various feature combinations and sub-combinations described in the detailed description.

BRIEF DESCRIPTION OF THE DRAWINGS

The accompanying drawings, which are incorporated in and constitute a part of this disclosure, illustrate various aspects and embodiments of the present invention. In the drawings.

DETAILED DESCRIPTION

The following detailed description refers to the accompanying drawings. Wherever possible, the same or similar reference numbers are used in the drawings and the following description to refer to the same or similar elements. While aspects and embodiments of the invention may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the scope of the invention.

The terms "a," "an," and "the" are intended to include plural alternatives, e.g., at least one. For instance, the disclosure of "a layer," "a tablet die," etc., is meant to encompass one or more than one layer, tablet die, etc., unless otherwise specified.

All publications and patents mentioned herein are incorporated herein by reference for the purpose of describing and disclosing, for example, the constructs and methodologies that are described in the publications, which might be used in connection with the presently described invention. The publications discussed throughout the text are provided solely for their disclosure prior to the filing date of the present application. Nothing herein is to be construed as an admission that the inventors are not entitled to antedate such disclosure by virtue of prior invention.

Applicants disclose several types of ranges in the present invention. When Applicants disclose or claim a range of any type, Applicants' intent is to disclose or claim individually each possible number that such a range could reasonably encompass, including end points of the range as well as any sub-ranges and combinations of sub-ranges encompassed therein. For example, in an aspect of the invention, the density of the multilayer tablet can be in a range from about 1.2 to about 2 g/cc. By a disclosure that the density is in a range from about 1.2 to about 2 g/cc, Applicants intend to recite that the density can be any density in the range and, for example, can be about 1.2, about 1.3, about 1.4, about 1.5, about 1.6, about 1.7, about 1.8, about 1.9, or about 2 g/cc. Additionally, the density can be within any range from about 1.2 to about 2 g/cc (for example, the density is in a range from about 1.3 to about 1.9 g/cc), and this also includes any combination of ranges between about 1.2 and about 2 g/cc. Likewise, all other ranges disclosed herein should be interpreted in a similar manner.

Multilayer Tablets

Disclosed herein are multilayer and multicomponent tablets, with the layers of the tablet oriented horizontally, as opposed to vertically layered tablets that predominate in the marketplace. In one aspect of this invention, a horizontally layered tablet is provided, and in this aspect, the tablet can comprise a first layer, a second layer, and an interface between the first layer and the second layer; moreover, the tablet can be characterized by a density of at least about 1.2 g/cc. Importantly, in this aspect, the horizontally layered tablet has a density of greater than 1 g/cc and, therefore, the tablet sinks in water. In some aspects, the density of the tablet can be in a range from about 1.2 to about 2.4, from about 1.2 to about 2, from about 1.3 to about 2, from about 1.4 to about 2, from about 1.2 to about 1.9, from about 1.2 to about 1.8, from about 1.3 to about 1.9, from about 1.3 to about 1.8, from about 1.4 to about 1.9, or from about 1.4 to about 1.8 g/cc, and the like. Other appropriate ranges for the density of the horizontally layered tablet are readily apparent from this disclosure. Furthermore, multilayered tablets consistent with the present invention also can have any of the features, properties, or characteristics provided below and in any combination.

Figure 1:
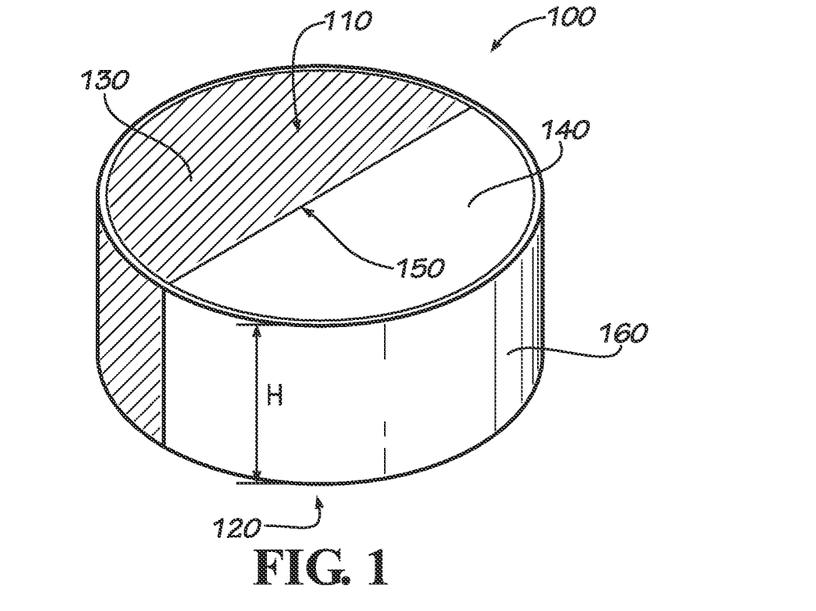
FIG. 1 is a top/front perspective view of a multilayer tablet in an aspect of the present invention.

In accordance with particular aspects of this invention, the tablet can have a width (i.e., the horizontal dimension; diameter if a circular cross-section) of the tablet that is greater than the height (i.e., the vertical dimension) of the tablet. This dimensional relationship is illustrated in FIG. 1, which shows a multilayer tablet 100 having a width (diameter) that is greater than the height H of the tablet 100. In reference to FIG. 1, the tablet 100 can have a top surface 110 and a bottom surface 120 (not visible in FIG. 1), a first layer 130, a second layer 140, an interface 150 between the layers, and a side surface 160.

In circumstances where the width is greater than the height, the ratio of these dimensions can vary over a fairly wide range, such as from about 1.2:1 to about 10:1. Alternatively, the ratio of the width of the tablet to the height of the tablet can be in a range from about 1.2:1 to about 8:1; alternatively, from about 1.2:1 to about 5:1; alternatively, from about 1.5:1 to about 7:1; alternatively, from about 1.5:1 to about 5:1; alternatively, from about 1.5:1 to about 4:1; alternatively, from about 1.5:1 to about 3:1; alternatively, from about 1.8:1 to about 6:1, or alternatively, from about 2:1 to about 5:1. Other appropriate ranges for the width:height ratio of the horizontally layered tablet are readily apparent from this disclosure.

In accordance with certain aspects of this invention, the tablet can be configured such that the major axis of the interface is greater than the height of the tablet. For instance, if the interface is elliptical in shape, the major axis is the longest diameter than runs through the center of the ellipse. As another example, if the interface is rectangular, the major axis is the longer of the width and the height; in FIG. 1, the width is the greater dimension, and is greater than the height of the tablet.

The multilayer tablet is not limited to any particular geometry. However, certain geometric features and shapes are specifically contemplated herein. In one aspect, for instance, the interface between the layers can be substantially perpendicular to the top of the tablet and/or substantially perpendicular to the bottom of the tablet. As used herein, "substantially perpendicular" is meant to indicate an angle of about 90°, for example, from about 75° to about 105°, between the interface and the top of the tablet and/or between the interface and the bottom of the tablet. In another aspect, a cross-section perpendicular to the interface of the multilayer tablet can be of any suitable geometric shape, non-limiting examples of which can include circular, elliptical or oval, rectangular, or square, and the like. In yet another aspect, the tablet can be in the shape of a disk or puck, for example, similar to a hockey puck.

Often, the interface between layers is generally linear, however, this is not a requirement. For instance, the interface can be non-linear, such as a curvilinear shape or S-shape.

While not being limited thereto, the volume of the first layer, based on the volume of the tablet, typically can be in a range from about 10 to about 90%; alternatively, from about 25 to about 75%; alternatively, from about 30% to about 70%; alternatively, from about 35% to about 65%; or alternatively, from about 40 to about 60%.

The first layer and the second layer can appear the same (e.g., but with a different composition), or can have a different visual appearance. For instance, the first layer can have a first color, and the second layer have a second color, and the first color and the second color can be different.

In accordance with alternative aspects of this invention, multilayer tablets are contemplated in which the ratio of the width of the tablet to the height of the tablet is from about 0.33:1 to about 0.8:1, such as, for example, from about 0.4:1 to about 0.8:1, from about 0.4:1 to about 0.75:1, or from about 0.45:1 to about 0.7:1. Other appropriate ranges for the width:height ratio of a multilayer tablet in this aspect of the invention are readily apparent from this disclosure.

Tablets of this invention often can have a hardness (or break strength) in a range from about 10 to about 500, from about 10 to about 475, from about 15 to about 500, from about 10 to about 50, or from about 150 to about 500 $lb_f$. The hardness is the force required to break the tablet when the tablet is placed on its side surface and the force applied to the directly opposing side surface. Unlike extruded or molded tablets, the tablets disclosed herein have a distinct break in aspects of this invention. Additionally or alternatively, the tablets disclosed herein, in particular aspects of this invention, do not have a vicat softening point or a glass transition temperature. These characteristics are typically related to extruded or molded tablets, which have a polymeric or plastic component in the tablet matrix. Thus, as distinguished from extruded tablets and molded tablets, the multilayer tablets disclosed herein can be categorized as compacted tablets (or compressed tablets). The tablet hardness (or break strength) depends upon the size of the tablet: a 3-inch diameter tablet can have a break strength that is 10-20 times that of a 1-inch diameter tablet.

Figure 2:
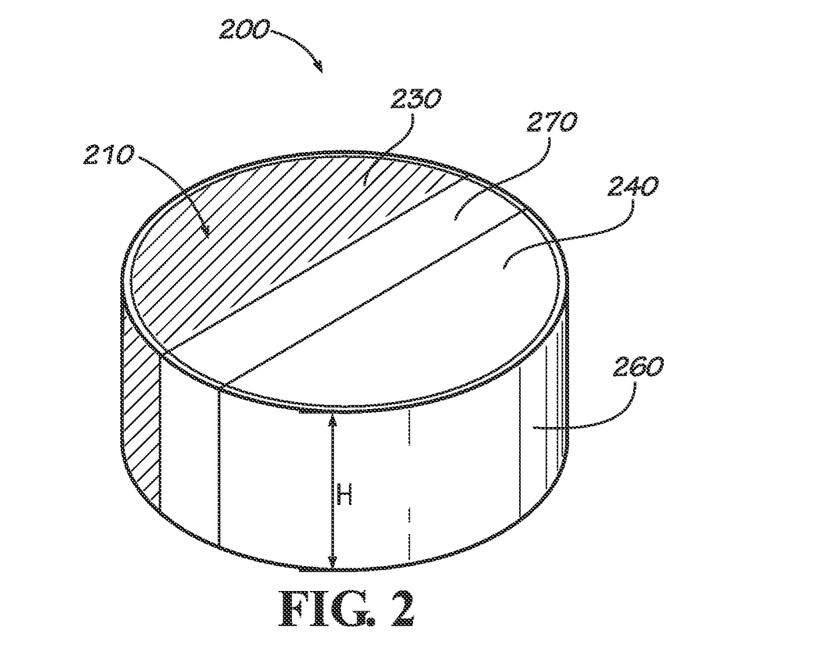
FIG. 2 is a top/front perspective view of a multilayer tablet in another aspect of the present invention.

Optionally, tablets disclosed herein can contain more than two layers. As shown in FIG. 2, a multilayer tablet 200 can have a third layer 270 (an intermediate layer, a barrier layer, etc.) between a first layer 230 and a second layer 240. The tablet 200 illustrated in FIG. 2 has a width (diameter) that is greater than the height H of the tablet 200. Similar to FIG. 1, the tablet 200 in FIG. 2 can have a top surface 210 and a bottom surface, interfaces between the layers, and side surface 260.

If desired, any of the tablets disclosed herein also can have a have an additional layer (a top layer) covering at least a portion of the top surface of the tablet. Additionally or alternatively, any of the tablets disclosed herein, optionally, can further comprise a coating layer (e.g., an enteric coating) on at least a portion of the outer surfaces of the tablet. This coating layer can cover the top surface, the bottom surface, the side surface, or all outer surfaces of the tablet.

In accordance with another aspect of this invention, tablets disclosed herein (e.g., horizontally layered tablets) can be characterized by a first layer comprising a first composition, a second layer comprising a second composition, an interface between the first layer and the second layer, and wherein the first composition and the second composition are different. In further aspects, such tablets can have any of the features, properties, or characteristics provided above (e.g., density, width:height ratio, hardness, layer ratio, etc.) and in any combination.

In aspects of this invention, the first composition and/or the second composition independently can comprise any suitable water treatment chemical, non-limiting examples of which can include a disinfectant, a sanitizer, a pH adjuster, a buffer, a hardness modifier, an algaecide, a corrosion inhibitor, a scale inhibitor, a dispersant, a flocculent, a clarifier, an oxidizer/shock, a sequestrant, a chelant, an emulsifier, a demulsifier, and the like, as well as combinations thereof. Accordingly, illustrative multilayer tablets can include: a tablet with a first layer containing a sanitizer, and a second layer containing an oxidizer/shock; a tablet with a first layer containing a sanitizer and a flocculent, and a second layer containing an oxidizer/shock and a flocculent; a tablet with a first layer containing a sanitizer and a flocculent, and a second layer containing an oxidizer/shock and a pH adjuster; a tablet with a first layer containing a sanitizer, a second layer containing an oxidizer/shock, and a third layer (intermediate layer) containing a flocculent; a tablet with a first layer containing a sanitizer, a second layer containing an oxidizer/shock, and a third layer (intermediate layer) containing a pH adjuster and a flocculent; a tablet with a first layer containing a corrosion inhibitor, and a second layer containing a scale inhibitor; a tablet with a first layer containing a corrosion inhibitor and a dispersant, and a second layer containing a scale inhibitor and a dispersant; and a tablet with a first layer containing a corrosion inhibitor, a second layer containing a scale inhibitor, and a third layer (intermediate layer) containing a dispersant. Hence, the first composition and/or the second composition independently can comprise, for example, a sanitizing composition, a shock composition, a clarifier composition, an algaecide composition, a pH or water hardness balancer composition, a corrosion control composition, a scale control composition, a cleaning composition, and the like, as well as any combination thereof. Information on such materials and compositions, as well as other suitable layer compositions, can be found, for example, in U.S. Pat. No. 6,426,317, which is incorporated herein by reference in its entirety (e.g., TCCA and a sodium or potassium salt of cyanuric acid). Other appropriate layer and composition selections for the multilayer tablet are readily apparent from this disclosure.

In another aspect, the first composition and/or the second composition independently can comprise any suitable halogenated (e.g., with active halogens such as chlorine and/or bromine) biological control agent, such as provided in U.S. Pat. Nos. 6,426,317, 6,852,238, and 8,492,419, the disclosures of which are incorporated herein by reference in their entirety. Illustrative compounds that can be used in the first layer and/or the second layer can include, but are not limited to, trichloroisocyanuric acid (TCCA), sodium dichloroisocyanurate (anhydrous, dihydrate salt), 1-bromo-3-chloro-5, 5-dimethylhydantoin, 1-chloro-3-bromo-5,5-dimethylhydantoin, 1-bromo-3-chloro-5-methyl-5-ethylhydantoin, 1-chloro-3-bromo-5-methyl-5-ethylhydantoin, 1-bromo-3-chloro-5,5-diethylhydantoin, 1-chloro-3-bromo-5,5-diethylhydantoin, 1-bromo-3-chloro-5-ethyl-5-methylhydantoin, 1-chloro-3-bromo-5-ethyl-5-methylhydantoin, 1,3-dichloro-5-ethyl-5-methylhydantoin, 1,3-dibromo-5-ethyl-5-methylhydantoin, 1,3-dichloro-5-methyl-5-ethylhydantoin, 1,3-dibromo-5-methyl-5-ethylhydantoin, 1,3-dichloro-5,5-dimethylhydantoin, 1,3-dibromo-5,5-dimethylhydantoin, 1,3-dichloro-5,5-diethylhydantoin, 1,3-dibromo-5,5-diethylhydantoin, calcium hypochlorite, lithium hypochlorite, and the like, as well as combinations thereof. Solid chlorine donors and other strong oxidizers also are suitable ingredients.

The layered tablets of invention are not limited compositionally to the materials and components noted hereinabove. Notably, the first composition and/or the second composition independently can comprise any active pharmaceutical ingredient (API) or nutraceutical ingredient suitable for tableting, and this includes any suitable prescription or over-the-counter (e.g., acetaminophen, aspirin) pharmaceutical ingredient, as well as vitamins and other nutritional supplements that are suitable for tableting. As would be recognized by those of skill in the art, any of the tablets and the respective layers and compositions described herein can further contain suitable tablet excipients, such as binders, lubricants, disintegrators, and the like, as well as combinations thereof.

A potential benefit of the multilayer tablets can be a tailoring of different release profiles of the respective layers for different end-use applications. In one aspect, for example, the first layer can be a quick release layer (or immediate release, or fast dissolving). Additionally or alternatively, the second layer can be a slow release layer (or delayed release, or slow dissolving). As disclosed herein, the tablet can contain an intermediate layer (or third layer) between the first layer and the second layer; this intermediate layer can be an inert layer or a barrier layer, if desired, to prevent any reaction or interaction between components of the first layer with components of the second layer.

Producing Multilayer Tablets

Methods of making multilayer tablets also are provided herein. One such method for making a horizontally layered tablet having a first layer and a second layer can comprise (a) providing a first composition and a second composition; (b) simultaneously feeding a segregated flow of the first composition and the second composition to a tablet die; and (c) compressing the first composition and the second composition under sufficient pressure in the tablet die to the form the horizontally layered tablet. In this method, the first layer comprises the first composition and the second layer comprises the second composition. The tablets producing in accordance with this method can have any of the features, properties, materials, or characteristics of the tablets described hereinabove and in any combination.

In step (b), the segregated flow of the first composition and the second composition can be simultaneously fed to the tablet die. In one aspect, the segregated flow can be gravity fed, while in another aspect, the segregated flow can be force fed.

Advantageously, in particular aspects of this invention, the method for making the horizontally layered tablet can comprise a single compression step. Hence, in such aspects, the method does not comprise a pre-compression step in order to form the tablet. While not wishing to be bound by theory, Applicants believe that this method, which can involve only a single compression in step (c), can result in an increase in the production rate of the multilayer tablets.

In step (c), the first composition and the second composition are compressed under sufficient pressure in the tablet die to form the horizontally layered tablet. Typically, though not required, this step is conducted using mechanical or hydraulically driven compression. The amount of pressure needed to form the tablet can be readily determined by those of skill in art, and generally, the pressure to form the tablet is uniform between the first layer and the second layer (e.g., within specifications based on percent variability of a particular press when operated in single layer mode).

This method also can further comprise, after step (c), a step of ejecting the (compressed or compacted) tablet from the tablet die. Typically, the interface between the first layer and the second layer is generally perpendicular to the bottom of the tablet die, for example, an angle of about 90°, or from about 75° to about 105°, between the interface and the bottom of the tablet die.

Advantageously, in aspects of this invention, the method of making the horizontally layered tablet does not include an extrusion step, and/or a molding step, and/or an external heating step. For example, the tablet die can be at ambient temperature, where no external heating or cooling of the tablet die is either utilized or required.

Tableting Equipment

An apparatus suitable for forming the multilayer tablets disclosed and described herein also is provided. For instance, an apparatus for forming a horizontally layered tablet (the tablet having a first layer comprising a first composition and a second layer comprising a second composition) can comprise (i) a tablet die, (ii) a first feed chamber containing the first composition and a second feed chamber containing the second composition, (iii) a reciprocating and segmented feed device for simultaneously directing a segregated flow of the first composition from the first feed chamber and the second composition from the second feed chamber to the tablet die, and (iv) a compaction device for compressing the first composition and the second composition in the tablet die under sufficient pressure to form the horizontally layered tablet having the first layer and the second layer. The tablets produced using this apparatus can have any of the features, properties, materials, or characteristics of the tablets described hereinabove and in any combination.

Figure 3A:
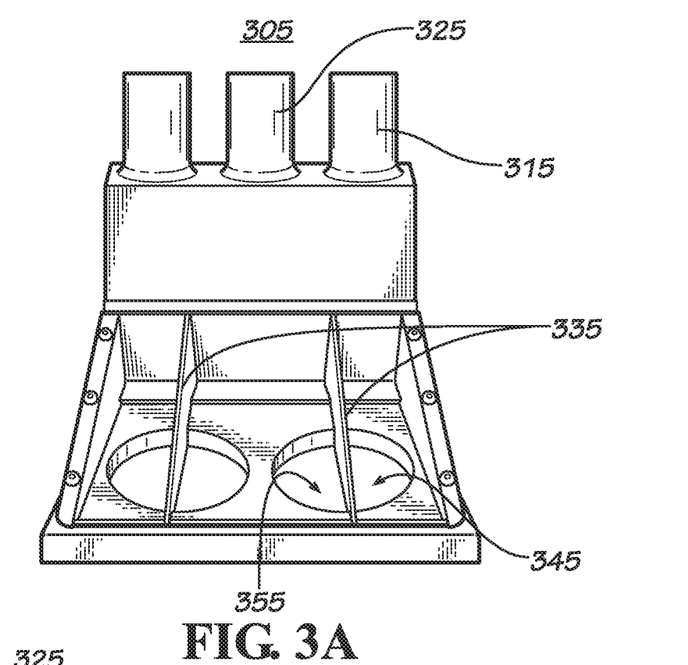
FIG. 3A is a top/front perspective view of a segmented feed device, with the top cover removed, in an aspect of the present invention.

FIGS. 3A-4C illustrate various components and views of the tableting apparatus. Referring first to FIGS. 3A-3C, in which different views of a feed device 305 (also referred to a feed shoe) are provided for a two-tablet (side-by-side) feed device. FIG. 3A is a top view of the feed device 305 in which the top cover is removed. The feed device 305 can have a first feed chamber 315, a second feed chamber 325, and dividers 335 for segmenting the flows from the feed chambers. A flow path of a first composition 345 from the first feed chamber 315 and a flow path of a second composition 355 from the second feed chamber 325 also are illustrated in FIG. 3A. The flows of the first composition and the second composition exit the bottom of the feed device and enter a tablet die, discussed further hereinbelow.

Figure 3B:
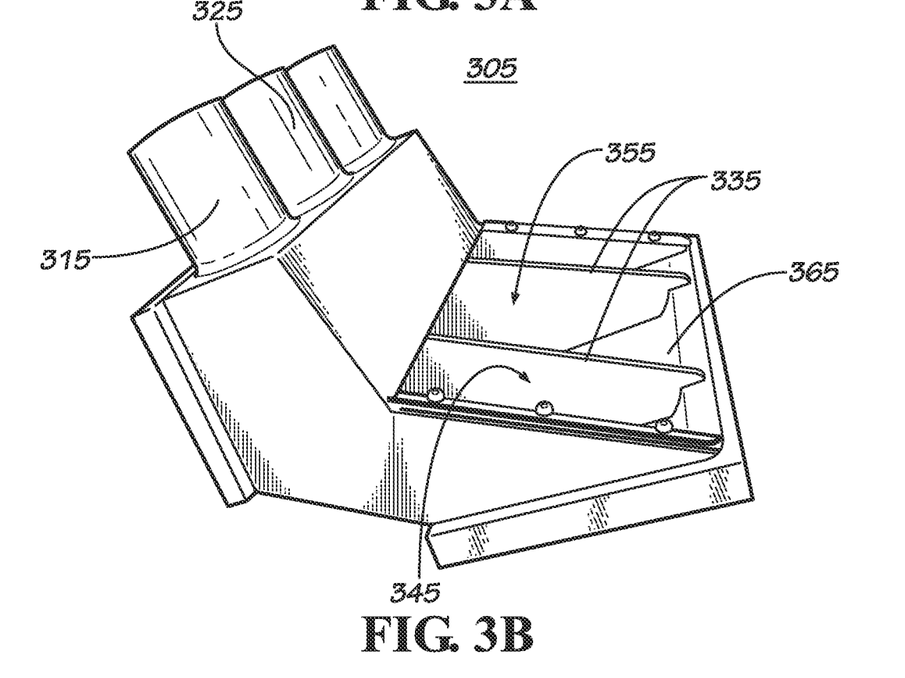
FIG. 3B is a side perspective view of the feed device of FIG. 3A with a clear top cover.
Figure 3C:
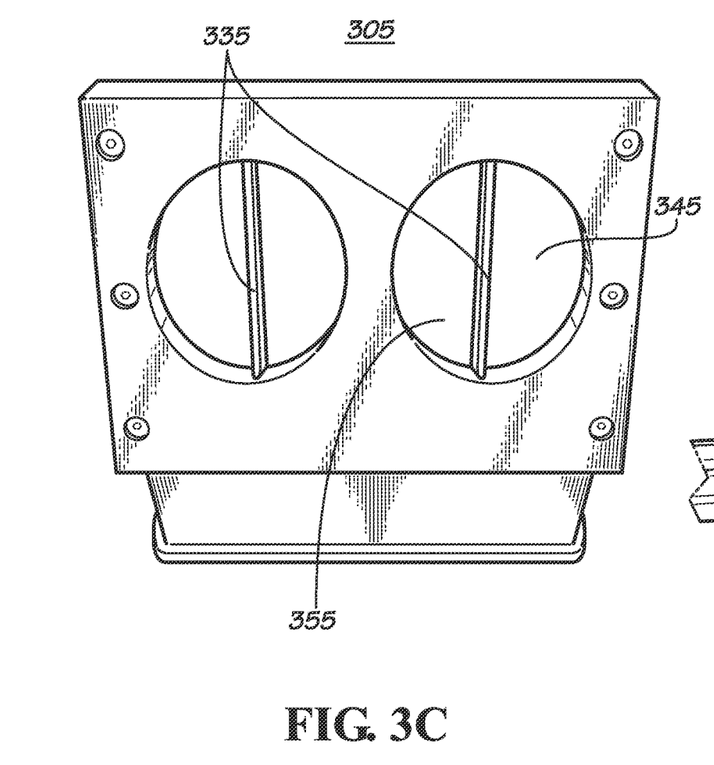
FIG. 3C is a bottom view of the feed device of FIG. 3A.

FIG. 3B is a side view of the feed device 305 with a clear top cover 365 (which can be any suitable plastic or metal material), and the respective locations are shown for the first feed chamber 315, the second feed chamber 325, the dividers 335 for segmenting the flows from the feed chambers, the flow path of the first composition 345 from the first feed chamber 315, and the flow path of the second composition 355 from the second feed chamber 325. FIG. 3C is a bottom view of the feed device 305, illustrating the dividers 335 for segmenting the flows from the feed chambers, the flow path of the first composition 345, and the flow path of the second composition 355.

Figure 4A:
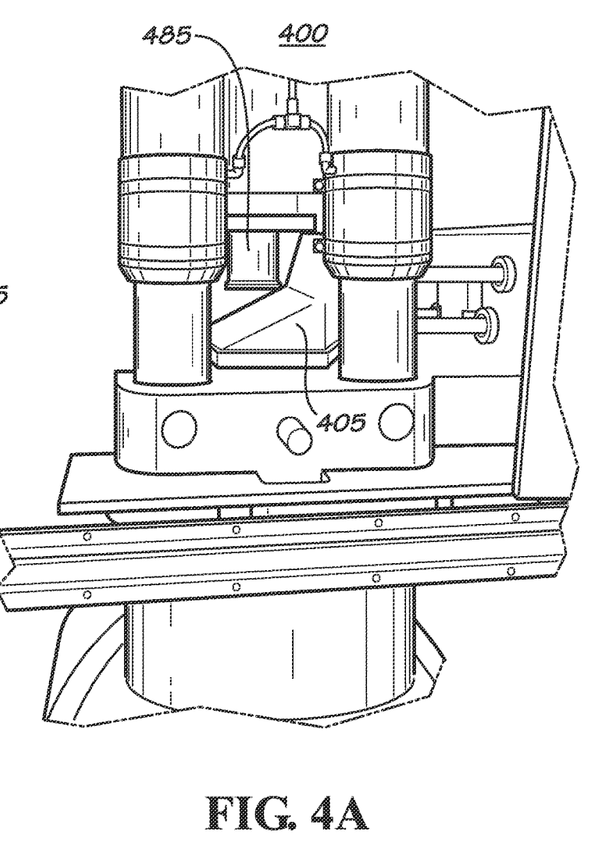
FIG. 4A is a side view of a tableting apparatus in the filling step.
Figure 4B:
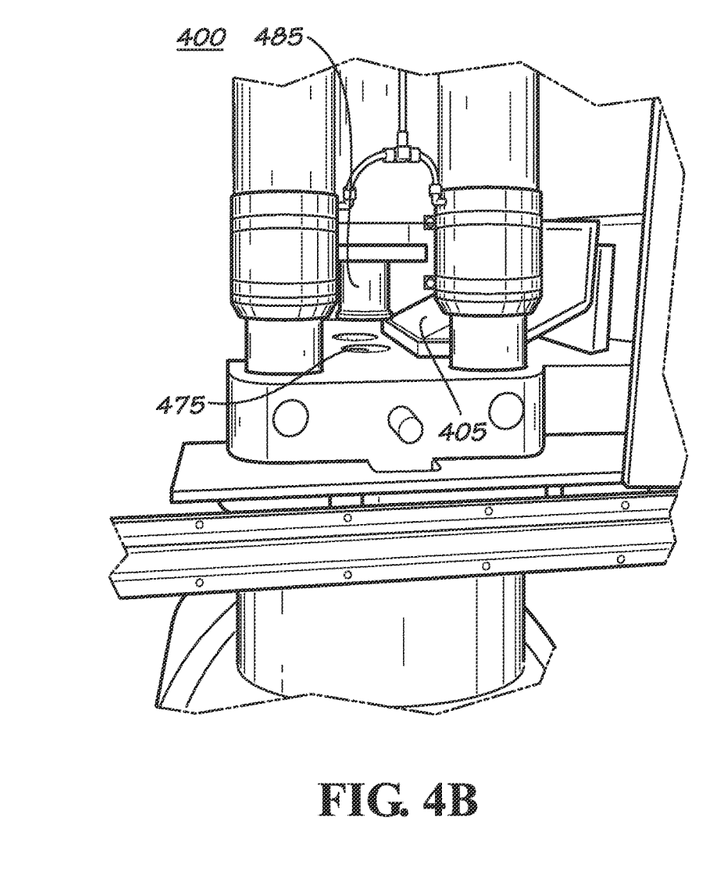
FIG. 4B is a side view of the tableting apparatus of FIG. 4A at the beginning of the compacting step.
Figure 4C:
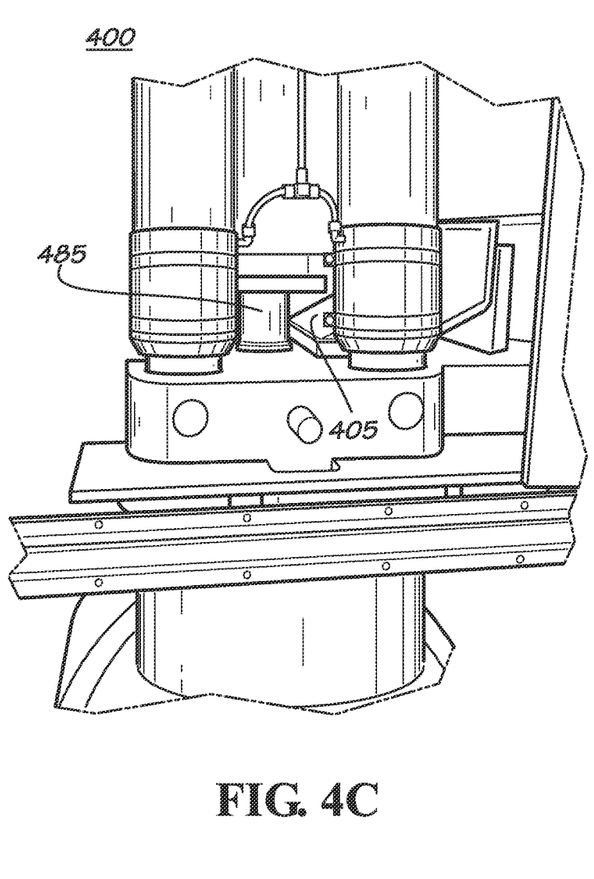
FIG. 4C is a side view of the tableting apparatus of FIG. 4A during the compacting step.

Referring now to FIGS. 4A-4C, which illustrate a side view of a tableting apparatus 400 during various stages of the cycle used to produce the multilayer tablets. In FIG. 4A, a compaction device 485 (or top punch) is retracted, and the feed device 405 (viewed from the side, with a metal top cover) is positioned over tablet dies (two side-by side, not shown in FIG. 4A), where the segmented flow of the first composition and the second composition fills each of the two tablet dies simultaneously, for example, to produce two tablets similar to the design and layout shown in FIG. 1. In FIG. 4B, the reciprocating feed device 405 retracts from the tablet dies 475 and the compaction device 485 proceeds in a downward motion toward the entrance of the tablet dies 475. The compaction device can be a mechanical compaction device or a hydraulic compaction device, as desired. In FIG. 4C, the compaction device 485 proceeds into the tablet dies to compress and compact the segmented first composition and second composition to form compacted horizontally layered tablets. Subsequently, the compaction device retracts, and the tablets are ejected from the tablet dies. For example, tablet ejection can be accomplished by an upward movement of a bottom punch.

The above-described figures illustrate an apparatus designed with 2 tablet dies. However, the apparatus can be configured with any suitable number of tablet dies, such as from 1 to 30, from 1 to 15, from 2 to 30, from 2 to 15, or from 2 to 10, and so forth. The depth of the tablet die(s) also is not particularly limited, and can be configured based on the desired height of the finished tablet(s). Typically, the tablet die(s) has/have a depth ranging from about 1/8" to about 10 inches, or from about 1/4" to about 6 inches.

As shown and described herein, the tableting apparatus in aspects of this invention is not a rotary tablet press, in which multilayer tablets are typically formed in a vertical and sequential fashion (i.e., one layer or composition on top of another layer or composition). Beneficially, however, due to the segregated and simultaneous flow of the respective compositions (and layers) in accordance with this invention, multilayer tablets can be formed at relatively high output rates. Generally, the tableting apparatus is capable of forming (horizontally layered) tablets in a output rate range, based on each tablet die, of from about 30 to about 70, from about 35 to about 65, or from about 40 to about 60 tablets/minute, and the like.

Also advantageously, the tableting apparatus does not require a heating or cooling system, as would be the case for extruded or molded tablets, in contrast with the compacted tablets produced in aspects of this invention.

The invention is further illustrated by the following examples, which are not to be construed in any way as imposing limitations to the scope of this invention. Various other aspects, embodiments, modifications, and equivalents thereof which, after reading the description herein, may suggest themselves to one of ordinary skill in the art without departing from the spirit of the present invention or the scope of the appended claims.

Examples 1-2

Horizontally layered tablets were produced using a Baldwin mechanical press with a reciprocating gravity feed shoe device to fill two tablet die cavities simultaneously. This feed shoe device was modified such that the two (2) separate feed streams could be fed simultaneously to the tablet die cavities in a fashion to produce a horizontally layered tablet where each layer received approximately equal amounts of the respective feed streams (50% in each layer). The horizontally layered tablets had a diameter of 3 inches, a height of 1¼ inches, and weighed about 8 ounces. Representative equipment used to produce the tablets is illustrated in FIGS. 3A-4C, and the tablet produced is generally illustrated by FIG. 1.

Two tablet combinations were produced. In Example 1, the same sanitizing, slow dissolving, formula designed to maintain oxidizing chlorine levels over a period of time was fed, except that one layer of the tablet was supplied an un-dyed (white) feed and the other layer was supplied a dyed (blue) feed to yield a horizontally layered tablet differentiated by appearance. The density of the tablets in Example 1 was 1.6 g/cm$^3$ and the tablet hardness (or break strength) was 430 lb$_f$. In Example 2, the un-dyed (white) sanitizing, slow dissolving feed used in Example 1 was fed simultaneously with a dyed (blue) shock, fast dissolving, feed intended for rapid delivery of oxidizing chlorine to yield a horizontally layered tablet differentiated by multi-functional delivery of incompatible components to recirculating water systems such as pools and spas. The density of the tablets in Example 2 was 1.55 g/cm$^3$ and the tablet hardness (or break strength) was 192 lb$_f$. The shape and design of the tablet products of Examples 1-2 are generally represented by the tablet illustration of FIG. 1. The compositions of the respective layers of the tablets of Examples 1-2 are provided in Table 1 below.

Unexpectedly, these tablets were manufactured at the same rate (48-49 tablets per minute, for each tablet die) as single component tablets of the same size and nominal composition, but with a clearly defined interface between the two layers. Moreover, this was accomplished on a tablet press designed only for single layer production without any loss of production rate. The tablets produced did not exhibit weakness along the layer interface and had similar mechanical properties (such as break strength) to single layer tablets produced on the same equipment having the same size and nominal composition.

TABLE 1

Examples 1-2.

| Example Number | Layer 1 | Layer 1 Composition | Layer 2 | Layer 2 Composition |
|---|---|---|---|---|
| 1 | White Sanitizing Layer | 99% TCCA- 95.2% SHMP - 3.8% Boric Acid- 1.0% | Blue Sanitizing Layer | 99% TCCA- 95.0% SHMP - 3.8% Boric Acid - 1.0% Blue Dye - 0.2% |
| 2 | White Sanitizing Layer | 99% TCCA- 95.2% SHMP - 3.8% Boric Acid- 1.0% | Blue Shock Layer | DCCA - 60.0% Sodium Sulfate - 19.8% Alum 10.0% Borax - 5.5% Boric Acid - 4.5% Blue Dye - 0.2% |

Notes on Table 1: 99% TCCA is 99% trichlorocyanuric acid, SHMP is sodium hexametaphosphate, Blue Dye is Pigment Blue 29, DCCA is sodium dichloroisocyanuric acid, Alum is aluminum sulfate (hydrated), and Borax is sodium tetraborate pentahydrate.

Examples 3-6

Horizontally layered tablets having a 1" diameter (and a height of 5/8") and weighing approximately 20 grams were produced using a laboratory press, where each layer received approximately equal amounts of the respective components (50% in each layer). Tablets were compressed for 30 sec at 10 kpsi, producing stable and robust multilayer tablets. The tablets produced are generally illustrated by FIG. 1. The compositions of the respective layers of the tablets of Examples 3-6 are provided in Table 2 below.

TABLE 2

Examples 3-6.

| Example Number | Layer 1 Composition | Layer 2 Composition |
|---|---|---|
| 3 | Alum and Blue Dye | MgSO$_4$*7H$_2$O |
| 4 | Alum and Blue Dye | CaCl$_2$ |
| 5 | Alum and Blue Dye | Na$_2$CO$_3$ |
| 6 | Alum and Blue Dye | NaHSO$_4$ |

Embodiments

The invention is described above with reference to numerous aspects and embodiments, and specific examples. Many variations will suggest themselves to those skilled in the art in light of the above detailed description. All such obvious variations are within the full intended scope of the appended claims. Other embodiments of the invention can include, but are not limited to, the following (embodiments are described as "comprising" but, alternatively, can "consist essentially of" or "consist of"):

Embodiment 1. A horizontally layered tablet comprising a first layer; a second layer; and an interface between the first layer and the second layer; wherein the tablet is characterized by a density of at least about 1.2 g/cc.

Embodiment 2. The tablet defined in embodiment 1, wherein the density of the tablet is in any range disclosed herein, e.g., from about 1.2 to about 2.4, from about 1.2 to about 2, from about 1.3 to about 2 g/cc, etc.

Embodiment 3. The tablet defined in embodiment 1 or 2, wherein the width (horizontal dimension; diameter if circular) of the tablet is greater than the height (vertical dimension) of the tablet.

Embodiment 4. The tablet defined in any one of the preceding embodiments, wherein a ratio of the width of the tablet to the height of the tablet is in any range disclosed herein, e.g., from about 1.2:1 to about 10:1, from about 1.5:1 to about 5:1, etc.

Embodiment 5. The tablet defined in any one of the preceding embodiments, wherein the major axis of the interface is greater than the height of the tablet.

Embodiment 6. The tablet defined in embodiment 1 or 2, wherein a ratio of the width of the tablet to the height of the tablet is in any range disclosed herein, e.g., from about 0.33:1 to about 0.8:1, from about 0.4:1 to about 0.75:1, etc.

Embodiment 7. The tablet defined in any one of the preceding embodiments, wherein the interface is substantially perpendicular to the top of the tablet and/or the bottom of the tablet.

Embodiment 8. The tablet defined in any one of embodiments 1-6, wherein the interface is generally linear.

Embodiment 9. The tablet defined in any one of embodiments 1-6, wherein the interface is a curvilinear shape (S-shape).

Embodiment 10. The tablet defined in any one of the preceding embodiments, wherein a cross-section perpendicular to the interface is any geometric shape disclosed herein, e.g., circular, elliptical/oval, rectangular, square, etc.

Embodiment 11. The tablet defined in any one of the preceding embodiments, wherein the tablet is in the shape of a disk or puck.

Embodiment 12. The tablet defined in any one of the preceding embodiments, wherein the tablet has a hardness in any range disclosed herein, e.g., from about 10 to about 500, from about 10 to about 50, from about 150 to about 500 $lb_f$, etc.

Embodiment 13. The tablet defined in any one of the preceding embodiments, wherein the tablet has a distinct break.

Embodiment 14. The tablet defined in any one of the preceding embodiments, wherein the tablet does not have a vicat softening point or a glass transition temperature.

Embodiment 15. The tablet defined in any one of the preceding embodiments, wherein the volume of the first layer, based on the volume of the tablet, is in any percentage range disclosed herein, e.g., from about 10 to about 90%, from about 25 to about 75%, from about 40 to about 60%, etc.

Embodiment 16. The tablet defined in any one of the preceding embodiments, wherein the first layer has a first color, and the second layer has a second color, and the first color and the second color are different.

Embodiment 17. The tablet defined in any one of the preceding embodiments, wherein the tablet further comprises a third layer (intermediate layer, barrier layer, etc.) between the first layer and the second layer.

Embodiment 18. The tablet defined in any one of the preceding embodiments, wherein the tablet further comprises a top layer on at least a portion of the top surface of the tablet.

Embodiment 19. The tablet defined in any one of the preceding embodiments, wherein the tablet further comprises a coating layer (e.g., an enteric coating) on at least a portion of the outer surfaces of the tablet.

Embodiment 20. The tablet defined in any one of the preceding embodiments, wherein the tablet is a compacted tablet, e.g., not an extruded tablet, not a molded tablet, etc.

Embodiment 21. A horizontally layered tablet comprising a first layer comprising a first composition; a second layer comprising a second composition; and an interface between the first layer and the second layer; wherein the first composition and the second composition are different.

Embodiment 22. The tablet defined in embodiment 21, wherein the tablet is further characterized as defined in any one of embodiments 1-20.

Embodiment 23. The tablet defined in embodiment 21 or 22, wherein the first composition and/or the second composition independently comprise any suitable water treatment chemical or any water treatment chemical disclosed herein, e.g., disinfectant, sanitizer, pH adjuster, buffer, hardness modifier, algaecide, corrosion inhibitor, scale inhibitor, dispersant, flocculent, clarifier, oxidizer/shock, sequestrant, chelant, emulsifier, demulsifier, etc., or combinations thereof.

Embodiment 24. The tablet defined in embodiment 21 or 22, wherein the first composition and/or the second composition independently comprise any suitable halogenated biological control agent or any halogenated biological control agent disclosed herein.

Embodiment 25. The tablet defined in embodiment 21 or 22, wherein the first composition and/or the second composition independently comprise a sanitizing composition, a shock composition, a clarifier composition, an algaecide composition, a pH or water hardness balancer composition, a corrosion control composition, a scale control composition, a cleaning composition, or any combination thereof.

Embodiment 26. The tablet defined in embodiment 21 or 22, wherein the first composition and/or the second composition independently comprise any active pharmaceutical ingredient or nutraceutical ingredient suitable for tableting or any active pharmaceutical ingredient or nutraceutical ingredient disclosed herein.

Embodiment 27. The tablet defined in any one of embodiments 21-26, wherein the tablet further comprises any suitable tablet excipient or any tablet excipient disclosed herein, e.g., binder, lubricant, disintegrator, etc.

Embodiment 28. The tablet defined in any one of embodiments 21-27, wherein the first layer is quick release layer, e.g., immediate release, fast dissolving, etc.

Embodiment 29. The tablet defined in any one of embodiments 21-28, wherein the second layer is a slow release layer, e.g., delayed release, slow dissolving, etc.

Embodiment 30. The tablet defined in any one of embodiments 21-29, wherein the tablet further comprises an intermediate layer between the first layer and the second layer, e.g., a barrier layer, an inert layer, etc.

Embodiment 31. A method of making a horizontally layered tablet having a first layer and a second layer, the method comprising providing a first composition and a second composition; simultaneously feeding a segregated flow of the first composition and the second composition to a tablet die; and compressing the first composition and the second composition under sufficient pressure in the tablet die to the form the horizontally layered tablet; wherein the first layer comprises the first composition and the second layer comprises the second composition.

Embodiment 32. The method defined in embodiment 31, wherein the tablet is further characterized as defined in any one of embodiments 1-30.

Embodiment 33. The method defined in embodiment 31 or 32, wherein the method comprises a single compressing step.

Embodiment 34. The method defined in any one of embodiments 31-33, wherein the method does not comprise a pre-compression step.

Embodiment 35. The method defined in any one of embodiments 31-34, wherein the segregated flow is gravity fed.

Embodiment 36. The method defined in any one of embodiments 31-34, wherein the segregated flow is force fed.

Embodiment 37. The method defined in any one of embodiments 31-36, wherein the compressing step comprises mechanical or hydraulically driven compression.

Embodiment 38. The method defined in any one of embodiments 31-38, further comprising a step of ejecting the tablet from the tablet die.

Embodiment 39. The method defined in any one of embodiments 31-38, wherein the method does not comprises an extrusion step and/or a molding step and/or an external heating step.

Embodiment 40. The method defined in any one of embodiments 31-39, wherein the tablet die is at ambient temperature, e.g., no external heating or cooling of the tablet die.

Embodiment 41. The method defined in any one of embodiments 31-40, wherein the sufficient pressure in the compressing step is uniform between the first layer and the second layer, e.g., within specifications based on percent variability of a particular press when operated in single layer mode.

Embodiment 42. The method defined in any one of embodiments 32-41, wherein the interface between the first layer and the second layer is generally perpendicular to the bottom of the tablet die.

Embodiment 43. An apparatus for forming a horizontally layered tablet having a first layer comprising a first composition and a second layer comprising a second composition, the apparatus comprising a tablet die; a first feed chamber containing the first composition and a second feed chamber containing the second composition; a reciprocating and segmented feed device for simultaneously directing a segregated flow of the first composition from the first feed chamber and the second composition from the second feed chamber to the tablet die; and a compaction device for compressing the first composition and the second composition in the tablet die under sufficient pressure to form the horizontally layered tablet having the first layer and the second layer.

Embodiment 44. The apparatus defined in embodiment 43, wherein the tablet is further characterized as defined in any one of embodiments 1-30.

Embodiment 45. The apparatus defined in embodiment 43 or 44, wherein the apparatus is not a rotary tablet press.

Embodiment 46. The apparatus defined in any one of embodiments 43-45, wherein the compaction device is a mechanical compaction device or a hydraulic compaction device.

Embodiment 47. The apparatus defined in any one of embodiments 43-46, wherein the compaction device comprises a downward movement of a top punch and/or an upward movement of a bottom punch.

Embodiment 48. The apparatus defined in any one of embodiments 43-47, wherein the apparatus is further configured to eject the tablet from the tablet die by upward movement of a bottom punch to eject the tablet.

Embodiment 49. The apparatus defined in any one of embodiments 43-48, wherein the apparatus does not comprise a heating or cooling system.

Embodiment 50. The apparatus defined in any one of embodiments 43-49, wherein the apparatus comprises 2 or more tablet dies, e.g., from 2 to 30, from 2 to 15, from 2 to 10, etc.

Embodiment 51. The apparatus defined in any one of embodiments 43-50, wherein the tablet die has a depth of from about ⅛" to about 10 inches.

Embodiment 52. The apparatus defined in any one of embodiments 43-51, wherein the apparatus is capable of forming tablets in any output rate range disclosed herein, based on each tablet die, e.g., from about 30 to about 70, from about 40 to about 60 tablets/minute, etc.

We claim:

1. A method of making a horizontally layered tablet having a first layer and a second layer, the method comprising:
providing a first composition and a second composition;
simultaneously feeding a segregated flow of the first composition and the second composition to a tablet die; and
compressing the first composition and the second composition under sufficient pressure in the tablet die to the form the horizontally layered tablet;
wherein the first layer comprises the first composition and the second layer comprises the second composition; the tablet has a density in a range from about 1.2 to about 2.4 g/cc; a ratio of the width of the tablet to the height of the tablet is in a range from about 1.5:1 to about 5:1; and a volume of the first layer, based on the volume of the tablet, is in a range from about 10 to about 90%.

* * * * *